(12) United States Patent
Kawashima

(10) Patent No.: US 11,959,863 B2
(45) Date of Patent: Apr. 16, 2024

(54) SHEET INSPECTION DEVICE

(71) Applicant: OMRON Corporation, Kyoto (JP)

(72) Inventor: Yuto Kawashima, Kyoto (JP)

(73) Assignee: OMRON Corporation, Kyoto (JP)

( * ) Notice: Subject to any disclaimer, the term of this patent is extended or adjusted under 35 U.S.C. 154(b) by 0 days.

(21) Appl. No.: 17/763,373

(22) PCT Filed: Mar. 11, 2020

(86) PCT No.: PCT/JP2020/010530
§ 371 (c)(1),
(2) Date: Mar. 24, 2022

(87) PCT Pub. No.: WO2021/070405
PCT Pub. Date: Apr. 15, 2021

(65) Prior Publication Data
US 2022/0373476 A1 Nov. 24, 2022

(30) Foreign Application Priority Data

Oct. 9, 2019 (JP) .................................. 2019-185922

(51) Int. Cl.
*G01N 21/892* (2006.01)
*G01N 33/2045* (2019.01)

(52) U.S. Cl.
CPC ....... *G01N 21/892* (2013.01); *G01N 33/2045* (2019.01)

(58) Field of Classification Search
CPC ............. G01N 21/956; G01N 21/8806; G01N 21/954; G01N 21/88; G01N 21/9501; G01N 21/95692; G01N 2021/9546; G01N 21/8851; G01N 21/8901; G01N 21/33; G01N 2021/9548; G01N 2021/8887; G01N 21/5907; G01N 21/89; G01N 21/94;
(Continued)

(56) References Cited

U.S. PATENT DOCUMENTS 6,741,727 B1 5/2004 Hirasawa
2012/0044344 A1 2/2012 Zheng

FOREIGN PATENT DOCUMENTS

CN 101887030 A * 11/2010 ............. G01N 21/88
CN 110390661 A * 10/2019 ......... G01N 21/3151
(Continued)

OTHER PUBLICATIONS

International Search Report issued in Intl. Appln. No. PCT/JP2020/010530 dated Jun. 9, 2020. English translation provided.
(Continued)

*Primary Examiner* — Michael P Stafira
(74) *Attorney, Agent, or Firm* — ROSSI, KIMMS & McDOWELL LLP

(57) ABSTRACT

Provided is a sheet inspection device capable of saving space, reducing member costs, and reducing the number of maintenance steps. A first light source Ls1 and a first inspection part S1 for inspecting a flaw on the front surface of a sheet and a second light source Ls2 and a second inspection part S2 for inspecting a flaw on the back surface of the sheet are disposed in such a positional relationship that when the sheet has a hole, the first inspection part S1 can detect light emitted by the second light source and transmitted through the hole in the sheet.

3 Claims, 2 Drawing Sheets

(58) Field of Classification Search
CPC ... G01N 2021/3148; G01N 2021/5969; G01N 2021/8411; G01N 2021/8578; G01N 21/01; G01N 21/894; G01N 21/95; G01N 2201/0627; G01N 2201/0691; G01N 2021/95638; G01N 2021/95653; G01N 21/51; G01N 21/532; G01N 21/892; G01N 2201/061; G01N 2021/7786; G01N 2021/8845; G01N 21/78; G01N 21/8483; G01N 21/898; G01N 21/952; G01N 21/95684; G01N 33/2045; G01N 2021/8841; G01N 2021/9513; G01N 2021/95676; G01N 21/55; G01N 21/909; G01N 21/95607; G01N 2223/611; G01N 23/223; G01N 23/2251; G01N 2021/0112; G01N 2021/1787; G01N 2021/7759; G01N 2021/8812; G01N 2021/8848; G01N 2021/9586; G01N 21/00; G01N 21/21; G01N 21/4795; G01N 21/958; G01N 2201/0221; G01N 2201/127; G01N 23/225; G01N 2333/904; G01N 27/3272; G01N 27/3274; G01N 33/487; G01N 33/48771; G01N 33/49; G01N 2021/845; G01N 2021/8816; G01N 2021/8825; G01N 2021/8829; G01N 2021/8838; G01N 2021/8918; G01N 2021/8924; G01N 21/274; G01N 21/35; G01N 21/3563; G01N 21/453; G01N 21/4788; G01N 21/64; G01N 21/76; G01N 21/85; G01N 21/8903; G01N 21/9036; G01N 21/9515; G01N 33/025; G01N 33/442; G01N 2021/6419; G01N 2021/6421; G01N 2021/8835; G01N 2021/887; G01N 2035/00108; G01N 21/05; G01N 21/25; G01N 21/255; G01N 21/553; G01N 21/636; G01N 21/6428; G01N 21/658; G01N 21/77; G01N 21/8803; G01N 21/8916; G01N 21/93; G01N 21/9505; G01N 2201/0639; G01N 33/205; G01N 33/52; G01N 33/53; G01N 33/533; G01N 33/54366; G01N 33/54388; G01N 33/558; G01N 33/582; G01N 33/68; G01N 35/00029; G01N 1/30; G01N 2021/0181; G01N 2021/058; G01N 2021/1734; G01N 2021/4166; G01N 2021/4173; G01N 2021/458; G01N 2021/4735; G01N 2021/4742; G01N 2021/4752; G01N 2021/558; G01N 2021/6439; G01N 2021/6484; G01N 2021/7779; G01N 2021/8809; G01N 2021/8854; G01N 2021/8902; G01N 2021/8925; G01N 2021/945; G01N 2021/9542; G01N 2035/00435; G01N 2035/0448; G01N 2035/1037; G01N 21/13; G01N 21/278; G01N 21/3581; G01N 21/41; G01N 21/4133; G01N 21/45; G01N 21/4738; G01N 21/4785; G01N 21/552; G01N 21/59; G01N 21/6452; G01N 21/6458; G01N 21/7703; G01N 21/8983; G01N 21/9506; G01N 21/951; G01N 21/95623; G01N 2201/0612; G01N 2201/0614; G01N 2201/063; G01N 2201/0633; G01N 2201/0686; G01N 2201/0846; G01N 2201/103; G01N 2223/0566; G01N 2223/401; G01N 23/2055; G01N 33/36; G01N 33/5011; G01N 35/08; G01N 35/1002; G01N 35/1011; G01N 35/1065; G01N 35/1074; G01N 35/1079

See application file for complete search history.

(56) References Cited

FOREIGN PATENT DOCUMENTS

| | | | | |
|---|---|---|---|---|
| JP | 06026843 | A | * | 2/1994 |
| JP | H0626843 | A | * | 2/1994 |
| JP | H0626843 | A | | 2/1994 |
| JP | H07110307 | A | * | 4/1995 |
| JP | H09257720 | A | * | 10/1997 |
| JP | H11281588 | A | * | 10/1999 |
| JP | H11281588 | A | | 10/1999 |
| JP | 2000182052 | A | | 6/2000 |
| JP | 2001343331 | A | | 12/2001 |
| JP | 2010271133 | A | * | 12/2010 |
| JP | 2012526968 | A | | 11/2012 |
| JP | 2013205332 | A | * | 10/2013 |
| JP | 2015049213 | A | | 3/2015 |
| JP | 2017125805 | A | * | 7/2017 |

OTHER PUBLICATIONS

Written Opinion issued in Intl. Appln. No. PCT/JP2020/010530 dated Jun. 9, 2020. English translation provided.

Office Action issued in Japanese Appln. No. 2019-185922 mailed Feb. 13, 2024. English machine translation provided.

* cited by examiner

SHEET INSPECTION DEVICE

TECHNICAL FIELD

The present invention relates to a sheet inspection device.

BACKGROUND ART

Conventionally, as a sheet inspection device for inspecting a defect and a hole on front and back surfaces of a sheet-shaped inspection target material, there has been proposed a configuration including: two flaw defect inspection parts that inspect a flaw defect on the front surface side and a flaw defect on the back surface side of the inspection target material, respectively; and a transmitted-light-type hole defect inspection part that inspects a hole defect of the inspection target material (e.g., see Patent Document 1).

However, in a case where an optical inspection device is adopted as the flaw defect inspection device, the optical inspection device needs to be provided with a front light source and a back light source for irradiating the front and back surfaces of the inspection target material, respectively, and a front detector and a back detector for detecting reflected light from the inspection target material, which is the light emitted from the front light source and the back light source, respectively. Thus, in the sheet inspection device, together with a transmission light source for detecting a hole in the inspection target material and a hole detector for detecting light emitted from the transmission light source and transmitted through the hole, it is necessary to dispose at least six elements.

However, in a case where such a sheet inspection device is incorporated into a part of another device or in some other case, a large space for the sheet inspection device needs to be enhanced, and this hinders reduction in the size of the entire device. In addition, a larger number of components of the sheet inspection device leads to an increase in cost and an increase in the number of maintenance steps.

PRIOR ART DOCUMENT

Patent Document

Patent Document 1: Japanese Unexamined Patent Publication No. 2001-343331

SUMMARY OF THE INVENTION

Problems to be Solved by the Invention

The present invention has been made in view of the above problems, and an object of the present invention is to provide a sheet inspection device capable of saving space, reducing member cost, and reducing the number of maintenance steps.

Means for Solving the Problem

The present invention for solving the above problems is a sheet inspection device including: a first light source configured to irradiate a first surface of a sheet-shaped inspection target material; a first inspection part configured to detect reflected light obtained by the first surface of the inspection target material reflecting the light emitted by the first light source; a second light source configured to irradiate a second surface of the inspection target material; and a second inspection part configured to detect reflected light obtained by the second surface of the inspection target material reflecting the light emitted by the second light source, the sheet inspection device inspecting a defect of the inspection target material. The first inspection part is disposed at a position where, when the inspection target material has a hole, light emitted from the second light source and transmitted through the hole is detectable.

According to the present invention, the second light source for irradiating the back surface of the sheet with a light beam in order to inspect a defect on the second surface of the sheet also functions as a light source for inspecting a hole in the sheet, and the first inspection part for inspecting a defect on the first surface of the sheet also functions as a hole inspection part for inspecting a hole in the sheet. Hence a unique light source and inspection part for inspecting a hole in the sheet can be omitted. As thus described, the number of members of the sheet inspection device can be reduced, so that space saving and cost reduction can be realized, and the number of maintenance steps can be further reduced.

Further, in the present invention, the first inspection part may detect regularly reflected light obtained by the first surface regularly reflecting the light emitted by the first light source, and the second inspection part may detect regularly reflected light obtained by the second surface regularly reflecting the light emitted by the second light source.

According to this, it is possible to accurately inspect defects on the first surface and the second surface of the sheet.

Further, in the present invention, an incidence angle of the light emitted by the first light source and a reflection angle of the regularly reflected light detected by the first inspection part may both be set to 10±5 degrees, and an incidence angle of the light emitted by the second light source and a reflection angle of regularly reflected light detected by the second inspection part may both be set to 10±5 degrees.

According to this, it is possible to reliably inspect the presence or absence of a small hole in a thin inspection target material.

Effect of the Invention

According to the present invention, it is possible to provide a sheet inspection device capable of saving space, reducing member cost, and reducing the number of maintenance steps.

MODE FOR CARRYING OUT THE INVENTION

Application Example

Hereinafter, an application example of the present invention will be described with reference to the drawings.

Figure 1:
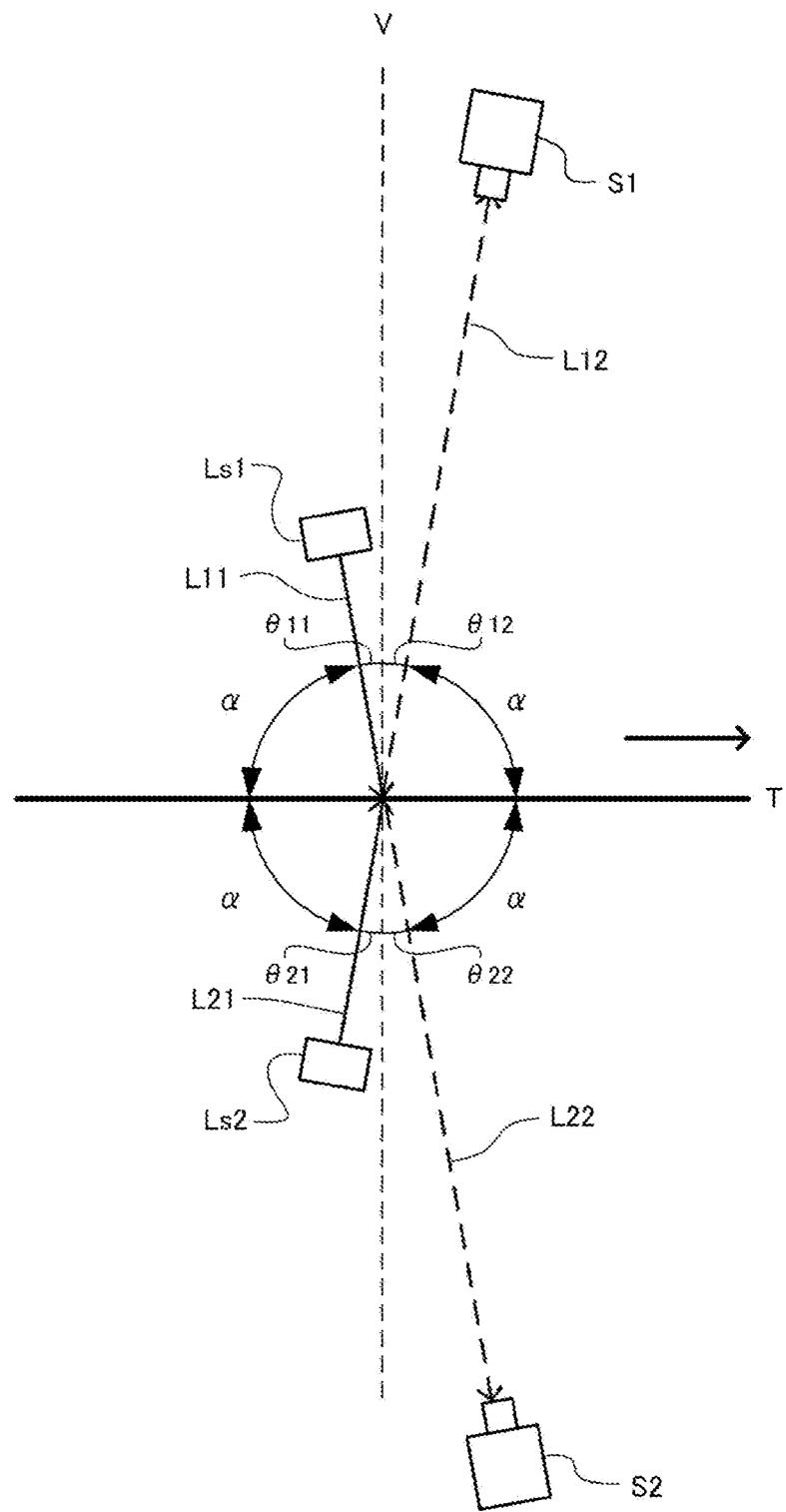
FIG. 1 is a diagram illustrating a main configuration of an inspection device according to an embodiment of the present invention.

In the present invention, as illustrated in FIG. 1, a first light source Ls1 and a first inspection part S1 for inspecting a flaw on the front surface of a sheet and a second light source Ls2 and a second inspection part S2 for inspecting a flaw on the back surface of the sheet are disposed in such a positional relationship that when the sheet has a hole, the first inspection part S1 can detect light emitted by the second light source and transmitted through the hole in the sheet.

This eliminates the need to provide a light source and an inspection part for detecting a hole in the sheet separately from the first light source, the first inspection part, the second light source, and the second inspection part for inspecting flaws on the sheet. As thus described, according to the present invention, the number of members of the sheet inspection device 1 can be reduced, so that space saving and cost reduction can be achieved, and the number of maintenance steps can be further reduced.

First Embodiment

Hereinafter, a sheet inspection device 1 according to an embodiment of the present invention will be described in more detail with reference to the drawings.

<Device Configuration>

FIG. 1 illustrates a main configuration of a sheet inspection device 1 according to the embodiment.

In FIG. 1, a sheet conveyance path T for conveying a sheet such as a steel plate, which is a sheet-shaped inspection target material, is formed so as to convey the sheet in a horizontal direction (from left to right on the paper (drawing)). Further, the sheet conveyance path T has an extension along the width direction of the sheet in a direction orthogonal to the conveyance direction (a direction orthogonal to the paper, from the front side to the back side of the paper). Although not illustrated, the sheet is supported by a conveyance device such as a conveyor and conveyed along the sheet conveyance path T.

When a light beam emitted from the first light source Ls1 on the front surface side of the sheet (the upper side of the paper) to the sheet is incident at an upward angle of α degrees with respect to the sheet conveyance path T, the first inspection part S1 on the front surface side of the sheet is disposed such that a light beam (regularly reflected light) incident from the first light source Ls1 and regularly reflected by the sheet, that is, a light beam reflected at an upward angle of α degrees with respect to the sheet conveyance path T is incident. As thus described, an incidence angle $\theta 11$ and a reflection angle $\theta 12$, which are angles formed by an optical path L11 from the first light source Ls1 to the sheet and an optical path L12 of light reflected by the sheet to the first inspection part S1 with respect to a vertical plane V orthogonal to the sheet conveyance path T (a plane orthogonal to the paper, from the front side to the back side of the paper), are both at positions of plane symmetry with respect to each other with an angle of 90−α degrees. In the sheet inspection device 1 to be described later, the first inspection part S1 detects the light irradiated by the first light source Ls1 and reflected by the front surface of the sheet as thus described, whereby the presence or absence of a flaw as a defect on the front surface of the sheet is inspected. The first inspection part S1 is disposed so as to detect the regularly reflected light of the light emitted by the first light source Ls1, so that it is possible to accurately detect a defect on the sheet. Here, the front surface of the sheet corresponds to the "first surface" of the present invention.

The second light source Ls2 on the back surface side of the sheet (the lower side of the paper) is disposed such that a light beam emitted from the second light source Ls2 is incident at a downward angle of α degrees with respect to the sheet conveyance path T. Then, the second inspection part S2 on the back surface side of the sheet is disposed such that a light beam (regularly reflected light) incident from the second light source Ls2 and regularly reflected by the sheet, that is, a light beam reflected at a downward angle of α degrees with respect to the sheet conveyance path T is incident. As described above, an incidence angle $\theta 21$ and a reflection angle $\theta 22$, which are angles formed by an optical path L21 from the second light source Ls2 to the sheet and an optical path L22 of light reflected by the sheet to the second inspection part S2 with respect to a vertical plane V orthogonal to the sheet conveyance path T, are both at positions of plane symmetry with respect to each other with an angle of 90−α degrees. In the sheet inspection device 1 to be described later, the second inspection part S2 detects the light emitted by the second light source Ls2 and reflected by the back surface of the sheet as thus described, whereby the presence or absence of a flaw as a defect on the back surface of the sheet is inspected. The second inspection part S2 is disposed so as to detect regularly reflected light of the light emitted by the second light source Ls2, so that it is possible to accurately detect a defect on the sheet. Here, the back surface of the sheet corresponds to the "second surface" of the present invention.

Here, the second light source Ls2 is disposed such that, when a light beam emitted from the second light source Ls2 to the sheet is transmitted to the front surface side due to the sheet having a hole, the light beam emitted from the second light source Ls2 is incident on the first inspection part S1. As thus described, in the sheet inspection device 1 to be described later, the first inspection part S1 detects the light emitted by the second light source Ls2 and transmitted through a hole in the sheet, and thereby, the presence or absence of a hole as a defect of the sheet is inspected. In the sheet inspection device 1 of the embodiment, when $\theta 11=\theta 12=\theta 21=\theta 22=10$ degrees (α=80 degrees), a hole having a diameter of 0.1 mm or more of a sheet with a thickness of 0.25 mm can be detected satisfactorily. It is preferable to set the angle $\theta 11$ (=$\theta 12=\theta 21=\theta 22$) to 10±5 degrees, and this makes it possible to satisfactorily detect a hole of a sheet with a thickness of 0.20 to 0.30 mm. It is more preferable to set $\theta 11$ (=$\theta 12=\theta 21=\theta 22$) to 10±1 degrees. In the configuration described above, when the sheet has a hole, a light beam emitted from the first light source Ls1 to the sheet is transmitted through the sheet and is incident on the second inspection part S2.

As thus described, in the embodiment, the second light source Ls2 that irradiates the back surface of the sheet with a light beam in order to inspect a flaw on the back surface of the sheet also functions as a light source for inspecting a hole in the sheet, and the first inspection part S1 for inspecting a flaw on the front surface of the sheet also functions as a hole inspection part for inspecting a hole in the sheet. Hence a unique light source and inspection part for inspecting a hole in the sheet can be omitted. As thus described, according to the embodiment, the number of members of the sheet inspection device 1 can be reduced, so that space saving and cost reduction can be realized, and the number of maintenance steps can be further reduced.

Here, each of the first light source Ls1 and the second light source Ls2 is a linear light source having an extension in a direction orthogonal to the conveyance direction (a direction orthogonal to the paper, from the front side to the back side of the paper) in order to irradiate a sheet having a width in the direction orthogonal to the conveyance direction. The linear light source may be, for example, a light source in which a plurality of light-emitting diode (LED) elements are arranged in the direction orthogonal to the conveyance direction and a diffusion plate is further provided, or may be a fluorescent lamp, and is not limited thereto.

The first inspection part S1 and the second inspection part S2 can use a line sensor camera having a visual field in a direction orthogonal to the conveyance direction so as to be able to detect light reflected or transmitted from a sheet having a width in the direction orthogonal to the conveyance direction.

Figure 2:
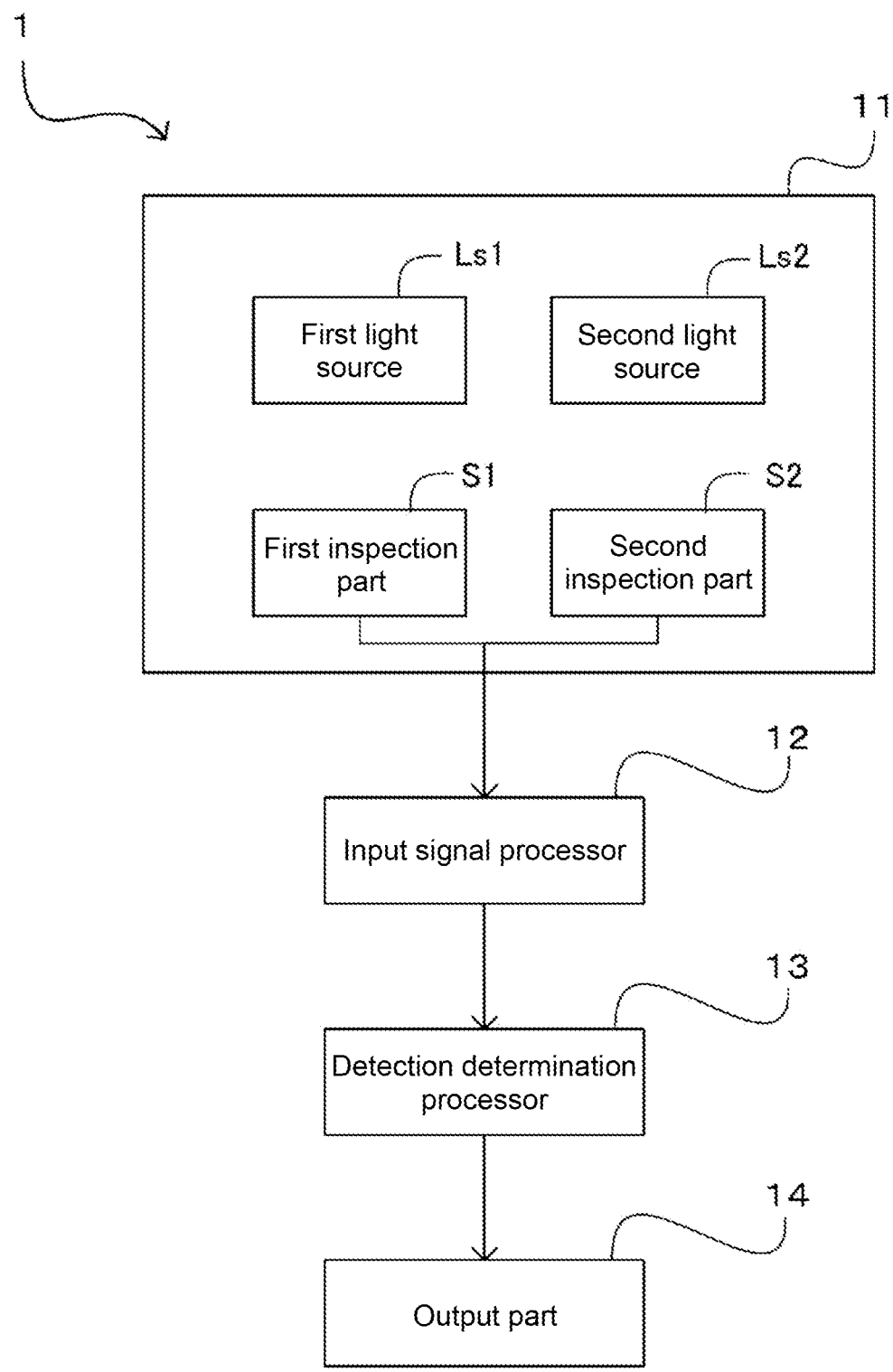
FIG. 2 is a functional block diagram of a sheet inspection device according to the embodiment of the present invention.

FIG. 2 is a functional block diagram of the sheet inspection device 1 according to the embodiment.

The sheet inspection device 1 includes an inspection part 11, an input signal processor 12, a detection determination processor 13, and an output part 14. The inspection part 11 includes the first light source Ls1, the first inspection part S1, the second light source Ls2, and the second inspection part S2.

The input signal processor 12 processes signals input from the first inspection part S1 and the second inspection part S2. For example, the input signal processor 12 includes an amplifier that amplifies electrical signals input from the first inspection part S1 and the second inspection part S2, a filter that cuts electrical noise, an analog-to-digital converter, a processor that performs image processing, and the like. As the input signal processor, a known technique can be appropriately adopted in accordance with the configuration of the inspection part.

The detection determination processor 13 detects and determines the presence or absence of a flaw, the type of the flaw, and the presence or absence of a hole on the basis of information output from the input signal processor 12. As the detection determination processor 13, a known technique can be appropriately adopted in accordance with the configurations of the inspection part 11 and the input signal processor 12.

The input signal processor 12 and the detection determination processor 13 can be formed of a computer including, for example, a central processing unit (CPU) and storage devices such as a read-only memory (ROM) and a random-access memory (RAM). By developing a program stored in the ROM or the like in the work area of the RAM or the like and executing the program in the CPU, it is possible to achieve each function matching a predetermined purpose. Each of the input signal processor 12 and the detection determination processor 13 may be achieved by a dedicated circuit such as a field-programmable gate array (FPGA) or an application-specific integrated circuit (ASIC).

The output part 14 outputs the processing result of the detection determination processor 13 to a notification unit, such as a display, a printer, a lamp, or a buzzer, or a marking device that marks the occurrence position of a flaw or a hole in the sheet.

<Modification>

In the sheet inspection device described above, when the sheet has a hole, the presence or absence of the hole in the sheet is inspected by the first inspection part S1 detecting light emitted by the second light source Ls2 and transmitted through the hole in the sheet. However, the presence or absence of the hole in the sheet may be inspected by the second inspection part S2 detecting light emitted by the first light source Ls1 and transmitted through the hole in the sheet. Further, the presence or absence of a hole in the sheet may be inspected using the result of the first inspection part S1 detecting the light emitted by the second light source Ls2 and transmitted through the hole in the sheet and the result of the second inspection part S2 detecting the light emitted by the first light source Ls1 and transmitted through the hole in the sheet.

In the following, the constituent elements of the present invention will be described with the reference numerals in the drawings in order to enable a comparison between the constituent elements of the present invention and the configurations of the embodiment.

<First Invention>

A sheet inspection device (1) including:
  a first light source (Ls1) configured to irradiate a first surface of a sheet-shaped inspection target material;
  a first inspection part (S1) configured to detect reflected light obtained by the first surface of the inspection target material reflecting the light emitted by the first light source (Ls1);
  a second light source (Ls2) configured to irradiate a second surface of the inspection target material; and
  a second inspection part (S2) configured to detect reflected light obtained by the second surface of the inspection target material reflecting the light emitted by the second light source (Ls2),
  the sheet inspection device (1) inspecting a defect of the inspection target material,
  in which the first inspection part (S1) is disposed at a position where, when the inspection target material has a hole, light emitted from the second light source (Ls2) and transmitted through the hole is detectable.

DESCRIPTION OF SYMBOLS 1 sheet inspection device
11 inspection part
12 input signal processor
13 detection determination processor
14 output part
Ls1 first light source
Ls2 second light source
S1 first inspection part
S2 second inspection part

The invention claimed is:

1. A sheet inspection device comprising:
a first light source configured to irradiate a first surface of a sheet-shaped inspection target material;
a first inspector configured to detect reflected light obtained by the first surface of the inspection target material reflecting the light emitted by the first light source;
a second light source configured to irradiate a second surface of the inspection target material;
a second inspector configured to detect reflected light obtained by the second surface of the inspection target material reflecting the light emitted by the second light source; and
a detection determination processor configured to detect and determine a defect of the inspection target material based on a signal input from the first inspector and/or a signal input from the second inspector,
wherein the first inspector is disposed at a position where, when the inspection target material has a hole, light emitted from the second light source and transmitted through the hole is detectable, and
the detection determination processor detects and determines the hole as the defect of the inspection target material in a case where the first inspector detects the light emitted from the second light source and transmitted through the hole.

2. The sheet inspection device according to claim 1, wherein
   the first inspector detects regularly reflected light obtained by the first surface regularly reflecting the light emitted by the first light source, and
   the second inspector detects regularly reflected light obtained by the second surface regularly reflecting the light emitted by the second light source.

3. The sheet inspection device according to claim 2, wherein
   an incidence angle of the light emitted by the first light source and a reflection angle of the regularly reflected light detected by the first inspector are both 10±5 degrees, and
   an incidence angle of the light emitted by the second light source and a reflection angle of regularly reflected light detected by the second inspector are both 10±5 degrees.

\* \* \* \* \*